United States Patent
Rimkus

[11] Patent Number: 6,015,293
[45] Date of Patent: Jan. 18, 2000

[54] ORAL CLEANING APPARATUS

[75] Inventor: Ronald J. Rimkus, Flossmoor, Ill.

[73] Assignee: AMTEC Products, Inc., Flossmoor, Ill.

[21] Appl. No.: 09/001,761

[22] Filed: Dec. 31, 1997

[51] Int. Cl.[7] ........................................... A61C 3/00
[52] U.S. Cl. ..................... 433/141; 132/309; 606/161; 15/111; 15/106
[58] Field of Search ........................ 132/308–310, 132/321–325, 329; 15/117, 110, 111, 160, 143.1, 167.1, 207.2, DIG. 6; 606/161; 601/139, 141, 142; 433/141

[56] References Cited

U.S. PATENT DOCUMENTS

| | | |
|---|---|---|
| D. 285,342 | 8/1986 | Audette . |
| D. 367,707 | 3/1996 | Baker . |
| D. 378,411 | 3/1997 | Taoatao . |
| D. 383,540 | 9/1997 | Woo . |
| 1,983,601 | 12/1934 | Conn . |
| 2,218,072 | 10/1940 | Runnels . |
| 2,491,274 | 12/1949 | McNeill . |
| 2,888,008 | 5/1959 | Rosenthal ................................. 601/141 |
| 3,943,592 | 3/1976 | Bhaskar et al. ........................... 15/160 |
| 4,079,478 | 3/1978 | Andrews, Sr. . |
| 4,488,327 | 12/1984 | Snider . |
| 4,582,059 | 4/1986 | Tiwari . |
| 4,638,521 | 1/1987 | Potente et al. ............................ 15/111 |
| 4,879,781 | 11/1989 | Desimone ................................. 15/110 |
| 5,005,246 | 4/1991 | Yen-Hui . |
| 5,061,272 | 10/1991 | Reese . |
| 5,205,302 | 4/1993 | Lemon et al. ............................ 132/321 |
| 5,217,475 | 6/1993 | Kuber . |
| 5,226,197 | 7/1993 | Nack et al. . |
| 5,282,814 | 2/1994 | Srivastava . |
| 5,339,480 | 8/1994 | Murg et al. ............................... 15/106 |
| 5,438,726 | 8/1995 | Leite ........................................ 15/105 |
| 5,530,981 | 7/1996 | Chen . |
| 5,569,278 | 10/1996 | Persad . |
| 5,604,951 | 2/1997 | Shipp ..................................... 15/167.1 |
| 5,613,262 | 3/1997 | Choy-Maldonado . |
| 5,735,864 | 4/1998 | Heisinger, Jr. .......................... 606/161 |
| 5,842,247 | 12/1998 | Decesare .................................. 15/106 |

*Primary Examiner*—Gene Mancene
*Assistant Examiner*—Pedro Philogene
*Attorney, Agent, or Firm*—Wallenstein & Wagner, Ltd.

[57] ABSTRACT

A disposable oral cleaning apparatus for cleaning and removing particles and bacteria from the upper surface of the tongue and between the teeth, including an elongated handle, a head component and a flexible connector connecting the elongated handle and the head component. The head component has a pre-cleaning portion, a cleaning portion and an absorbent portion to provide an initial cleaning of the coating of the tongue, a secondary deep cleansing of the pores of the tongue, and a final absorption and removal of all debris. The oral cleaning apparatus is adapted to promote proper cleansing of the tongue and teeth so as to eliminate oral bacteria and bad breath, to reduce tooth decay, gum disease and plaque buildup, and promote proper oral hygiene with no deleterious changes to the tongue.

21 Claims, 3 Drawing Sheets

ORAL CLEANING APPARATUS

TECHNICAL FIELD

The present invention relates generally to an oral cleaning apparatus for cleaning and medicating the surface of the tongue.

BACKGROUND OF THE INVENTION

Generally, brushing, flossing and rinsing with mouthwash have been standard methods utilized to eliminate oral bacteria and bad breath. According to studies, however, bacteria on the surface of the tongue can cause up to 75% of bad breath odor. As such, numerous devices have been conceived to try to remove bacterial growth on the surface of the tongue. Prior attempts to provide a means for cleaning the tongue generally fall into two categories: scraper-style cleaners and brush-style cleaners.

Scraper-style tongue cleaners are disclosed in U.S. Utility Pat. Nos. 5,438,726, 5,282,814, 5,005,246 and 2,218,072. Scraper-style tongue cleaners are also disclosed in U.S. Design Pat. Nos. Des. 367,707 and Des. 285,342.

U.S. Pat. No. 5,438,726 discloses a toothbrush having interchangeable periodontal devices, one being a concave tongue scraper. The tongue scraper is comprised of a single rigid blade.

U.S. Pat. No. 5,282,814 discloses an instrument for cleaning the top of the tongue. The instrument comprises a blade having a sharp, scraping edge to scrape any coating or other debris from the top of the tongue. The blade is connected to one or two rigid arms. This instrument, however, like the first disclosed, only has a single rigid blade to scrape away debris. As such, they do not allow for variations in the topographical surface of the tongue. Additionally, the rigid arm makes it difficult to administer an appropriate amount of pressure on the tongue.

U.S. Pat. No. 5,005,246 discloses a toothbrush having a tongue scaler slidably supported within the handle. The tongue scaler is used to remove the fur from the lingual body by bending the tongue scaler into a curved configuration and applying a reciprocating motion. Similar to the patents disclosed above, U.S. Pat. No. 5,005,246, discloses a single rigid blade to scrape away debris. This blade must be bent to fit within the mouth opening, making it difficult for the user to manipulate.

U.S. Design Pat. Nos. Des. 367,707 and Des. 285,342 disclose tongue cleaners/scrapers that are shaped similar to a common disposable razor. Each has a rigid handle with a single rigid blade. As such, both designs have every drawback of the above-mentioned patents.

Brush-style tongue cleaners are disclosed in U.S. Utility Pat. Nos. 5,613,262, 5,226,197, 4,079,478, 3,943,592 and 2,491,274. U.S. Pat. No. 5,613,262 discloses a device for cleaning the surface of the tongue comprising an elongated handle having a brush head attached to one end thereof. The handle has a slight angle. The handle, however, is rigid and does not allow for a variable pressure to be exerted on the tongue. Further, the brush head has a substantially flat surface and merely acts to brush food and debris from the surface of the tongue, similar to a toothbrush.

U.S. Pat. No. 5,226,197 discloses a tongue cleaning brush/scraper having a semi-rigid scraper and a plurality of short bristles. Like the above-mentioned scraper-style cleaners, this device only utilizes a single scraper. Further, the entire device is flat making it difficult for the user to properly clean the entire surface of the tongue.

U.S. Pat. No. 4,079,478 discloses a tongue brush. The brush, however, is large and cumbersome. Furthermore, the handle is larger yet, and awkward to maneuver. As such, this device may promote gaging and would, therefore, likely be ineffective.

U.S. Pat. No. 3,943,592 discloses a tongue cleaning device. This device is comprised of a VELCRO hook material attached to a flat member. However, this device only contains a single cleaning area. Also, like the devices described above, this device has the same deficiency in that it employs a flat-rigid handle.

U.S. Pat. No. 2,491,274 discloses a tongue cleaning device for cleaning the taste buds of the tongue and for the application of mouth wash. The device is comprised of a cleaning sponge which is of a porous-resilient nature and preferably formed from a single piece of rubber. The handle is a single rigid piece.

The above-described prior oral cleaning devices do not provide a means for collecting any saliva, food particles and bacteria that may be removed from the tongue during use of the apparatus. Thus, use of the above-described prior devices can be quite messy. Accordingly, the abovedescribed prior devices can usually be used only in limited circumstances and environments. In many instances, the prior devices are large, bulky and expensive to manufacture. The present invention is designed to solve these and other problems by providing a portable, disposable (either completely or partially) oral cleaning apparatus having an absorbent pad to catch saliva, food particles and bacteria as they are removed from the tongue.

SUMMARY OF THE INVENTION

Generally, the present invention provides an oral cleaning apparatus for cleaning and removing particles from the surface of the tongue. The oral cleaning apparatus is comprised of an elongated handle, a head component, and a flexible connector between the elongated handle and the head.

The elongated handle has a proximal end and a distal end. The elongated handle may also have a cavity adjacent the distal end. Further, the elongated handle may include a roughened surface or multiple surfaces around the handle for gripping the apparatus and an integral interproximal brush adjacent the distal end of the handle.

The head component has a first side and a second side. The head component further has a first section and a second section. Optionally, the head component may have a third section. The first section is generally comprised of a pre-cleaning portion; the second section is generally comprised of a cleaning portion; and, the third section is generally comprised of an absorbent portion. The first, second and third sections may either be located on the first side or second side of the head component. Additionally, the first, second and third sections may he located on both the first and second sides of the head component. In one embodiment the head component has multiple arcuate segments. In another embodiment, the head component has convex first and second sides.

The flexible connector enables the user to control the pressure exerted on the surface of the tongue by the apparatus, thus, avoiding any damage to the tongue. As such, the flexible connector is generally located between the proximal end of the handle and the head component.

The oral cleaning apparatus may also include a separate and detachable between-the-teeth cleaning utensil. The cleaning utensil is generally comprised of a brush and a holder. At least one brush is stored in the cavity of the elongated handle. The handle includes a multitude of vent holes allowing the brush to dry and thus avoiding a buildup of bacteria that could contaminate the brush if it were not permitted to properly dry.

In a first aspect of the present invention there is provided an oral cleaning apparatus which removes food particles and bacteria from the upper surface of the tongue by proffering an initial cleaning of the coating of the tongue, a secondary deep cleansing of the pores of the tongue, and a final absorption and removal of all debris.

In another aspect of the present invention there is provided an oral cleaning apparatus which medicates the surface of the tongue.

In yet another aspect of the present invention there is provided an oral cleaning apparatus which is designed to promote proper cleansing of the upper surface of the tongue while precluding a gag reflex.

In an additional aspect of the present invention there is provided an oral cleaning apparatus which can be easily and inexpensively manufactured such that portions of the apparatus, or the entire apparatus, may be disposable. As such the apparatus will be generally available to the entire public for use as part of their oral hygiene.

Other features and advantages of the invention will be apparent from the following specification taken in conjunction with the following drawings.

BRIEF DESCRIPTION OF THE DRAWINGS

In order that the present invention may be understood, it will now be described by way of example, with reference to the following drawings.

DETAILED DESCRIPTION OF THE PREFERRED EMBODIMENTS

Figure 1:
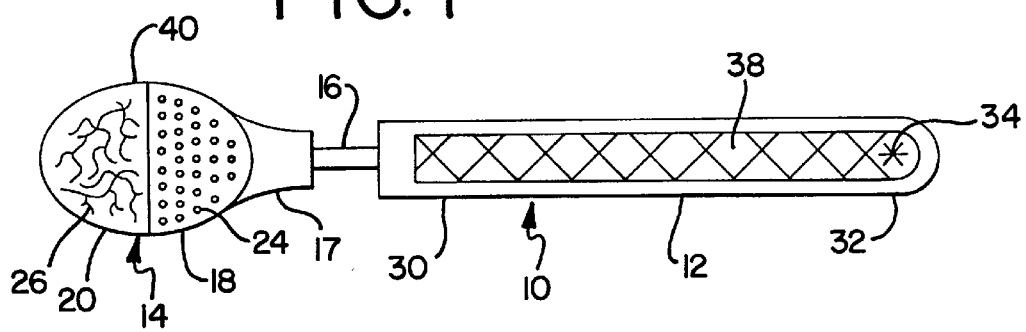
FIG. 1 is a plan view of an underside of an oral cleaning apparatus according to one embodiment of the present invention.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Figure 2:
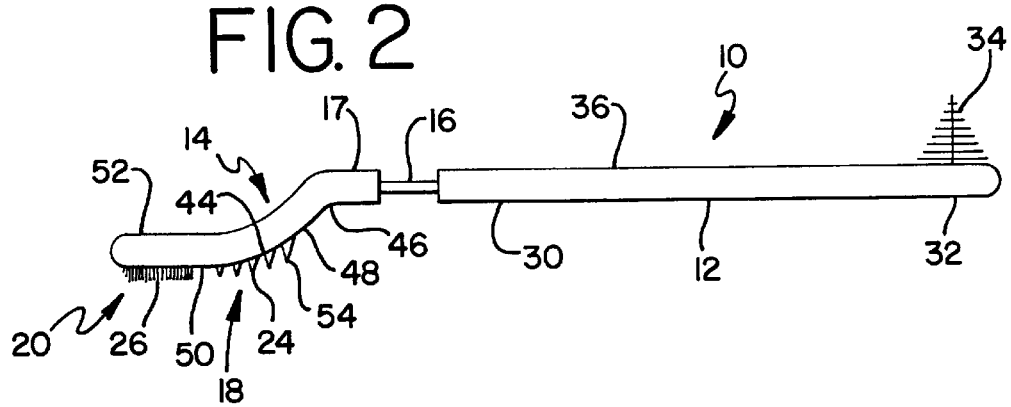
FIG. 2 is a side elevation view of the oral cleaning apparatus illustrated in FIG. 1.

Referring now in detail to the drawings and initially to FIGS. 1 and 2, there is shown a preferred embodiment of the oral cleaning apparatus 10 constructed in accordance with the present invention. The oral cleaning apparatus 10 preferably comprises an elongated handle 12, a head component 14, and a flexible connector 16 between the elongated handle 12 and the head component 14. The head component 14 illustrated in FIG. 1 has a first section 18 and a second section 20. The first section 18 is comprised of a cleaning portion 24 and the second section 20 is comprised of an absorbent portion 26. In operation, the head component 14, with cleaning and absorbent portions 24,26, is moved along the surface of the tongue, applying a slight downward pressure on the handle 12, in a posterior to anterior stroking motion. As the head 14 is moved along the surface of the tongue, the cleaning portion 24 removes the coating on the tongue including food particles and certain bacteria, while the absorbent portion 26 captures and carries away the removed coating (including food particles and certain bacteria), and provides a deep cleansing of the entire topography, including pores, of the tongue.

The elongated handle 12 is generally a rigid member and has a proximal end 30 and a distal end 32. Preferably, the handle 12 is made from a plastic material. Most preferably, the handle 12 is made from a medical grade plastic. An interproximal brush 34 extends from the distal end 32 of the handle 12. In the embodiment shown in FIG. 1, the interproximal brush 34 extends perpendicularly upward from the top surface 36 of the handle 12 and operates as an interdental cleaning device. The interproximal brush 34 is preferably formed from a plurality of bristles or molded plastic (e.g., nylon). In this embodiment, the interproximal brush 34 is permanently fixed to, and integral with, the handle 12. As is also represented in FIG. 1, the elongated handle 12 has a roughened surface or knurled area 38 on its top and bottom surfaces 36,38. The roughened surfaces 36,38 improve the ability to grip the apparatus 10 so that it does not slip in the user's hand. Preferably, the roughened surfaces 36,38 are molded directly into the handle 12 during manufacture of the handle 12.

The flexible connector 16 extends from the proximal end 30 of the handle 12 and connects a neck portion 17 of the head component 14 to the handle 12. The connector 16 is preferably made from a plastic strip, however, the connector 16 may also be made from a flexible metal or other flexible material. Further, the flexible connector 16 may be integral with the handle 12, the neck portion 17 of the head component 14, or both the handle 12 and the neck portion 17 of the head component 14. The connector 16 operates as a leaf spring or shock absorber between the handle 12 and the head component 14. As such, the flexible connector 16 provides a means for controlling the pressure exerted on the surface of the tongue. As the user pushes the handle 12 downward on the tongue with increased force, the flexible connector 16 bends or deforms resulting in a constant pressure on the tongue so as not to cause damage to the tongue. Additionally, the flexible connector 16 allows the head 14 to float on, and conform to, the topographical variations of the surface of the tongue. Accordingly, a larger portion of the head component 14 of the apparatus 10 maintains constant contact with the surface of the tongue as compared to prior apparatuses employing a single rigid scraping member.

As illustrated in the embodiment of FIG. 1, the head component 14 is connected to the flexible connector 16 via neck portion 17. The head component 14 comprises a circular or oval portion 40 and the neck portion 17 as seen in FIG. 1. As best displayed from the side view of FIG. 2, the head component 14 has arcuate segments 44,46 connecting an angular portion 48. The head component 14 further has a first side 50, a second side 52, a first section 18 comprised of a cleaning portion 24, and a second section 20 comprised of an absorbent portion 26.

Figure 3A:
FIGS. 3A–3C are side elevation views of cleaning projections according to several embodiments of the present invention.
Figure 3B:
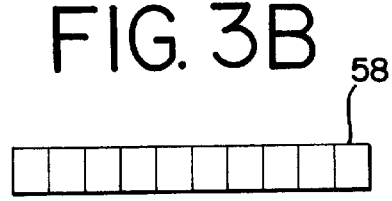
Figure 3C:
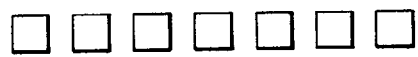
Figure 4A:
FIG. 4A is a top plan view of cleaning projections illustrated in FIG. 3A.
Figure 4B:
FIG. 4B is a top plan view of cleaning projections illustrated in FIG. 3B.
Figure 4C:
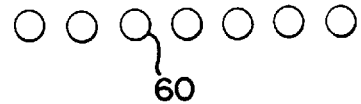
FIG. 4C is a top plan view of cleaning projections illustrated in FIG. 3C.

The cleaning portion 24 initially removes the coating on the surface of the tongue and provides a deep and thorough cleansing of the entire surface topography, including pores, of the tongue. In a preferred embodiment the cleaning portion 26 is comprised of a plurality of projections or cleaning fingers 54. The cleaning fingers or projections 54 are semi-rigid members which extend outwardly with respect to the first side 50 of the head 14. The projections 54 may be made of a VELCRO hook material as shown in FIG. 1, or of a molded plastic (not shown). The projections 54 may also include individual I-shaped projections 56 as shown in FIGS. 3A and 4A, individual rectangularly-shaped or square-shaped vertical members 58 as shown in FIGS. 3B and 4B, and individual cylindrically-shaped projections 60 as shown in FIGS. 3C and 4C. Each of the above-described projections 54 can be integral with, and possibly molded from the same material as that which comprises the head component 12. Alternatively, the projections 54 may be a separate element affixed to the second section 20 of the head component 14. As is shown in FIGS. 3 and 4, the projections 54 can be positioned ir a plurality of rows in the second section 20. All projections 54, no matter what the style, are independently and individually movable. When the projections 54 contact the surface of the tongue, they individually scrape the surface, moving back and forth according to the applied tangential and radial forces on the apparatus 10.

The absorbent portion 26 may be formed from a cellular, sponge-like material (e.g., reticulated polyurethane) or any other relatively soft, absorbent material (e.g., gauze, cotton, or the like).

In the embodiment shown in FIGS. 1 and 2, the first and second sections 18,20 are located on the first side 50 of the head 14. As such, the first side 50 is the side that is moved along the upper surface of the tongue to remove all debris from the upper surface of the tongue. Because the head 14 has flat, angled and arcuate sections, and both pre-cleaning and cleaning portions, the user can vary the cleaning from a minimum to maximum by raising or lowering the handle 12 with respect to the tongue accordingly.

Once the user has performed an appropriate number of cleaning strokes on the upper surface of the tongue, the head component 14 can be rinsed with hot water to remove the debris and prepare the apparatus 10 for the next usage. If the surface of the tongue is excessively soiled, a rinsing operation may be performed once or more between cleaning strokes. The oral cleaning apparatus 10 can be used numerous times before deterioration of the cleaning components 24,26 requires disposal of the apparatus 10.

Figure 5:
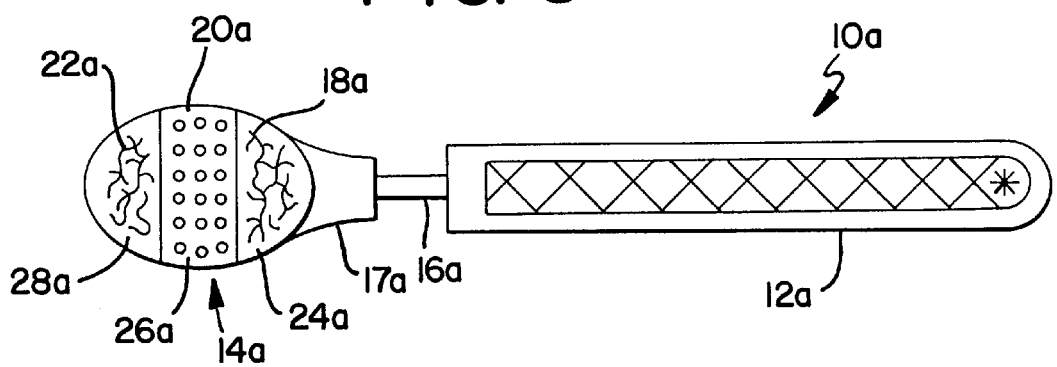
FIG. 5 is a plan view of an underside of an oral cleaning apparatus according to a second embodiment of the present invention.

Referring now to FIG. 5, in a second embodiment of the oral cleaning apparatus 10a of the present invention, the head component 14a is comprised of a first section 18a, a second section 20a, and a third section 22a. The first section 18a, immediately adjacent the neck portion 17a of the head 14a includes a pre-cleaning portion 24a comprised of a semi-abrasive material (e.g., wool or materials having a plurality of loops). One such material having a plurality of loops is a VELCRO loop material sold by the Velcro Corporation. The second section 18a is identical to and may be comprised of the same materials as the cleaning portion 26 of the embodiment illustrated in FIGS. 1 and 2. The third section 22a of the head component 14a comprises an absorbent portion 28a. The absorbent portion 28a is generally comprised of a soft pad or sponge which is attached to the third section 22a of the head component 14a. The absorbent portion 28a can also be comprised of a gauze material, reticulated polyurethane, cotton, or materials having a plurality of loops like the pre-cleaning portion 24. The absorbent portion 28a operates as a final pad to generally captivate debris, particles and bacteria which have been loosened from the surface of the tongue by the first and second sections 18a,20a, i.e., the pre-cleaning cleaning and cleaning portions 24a,26a of the head component 14a. Once captivated, the absorbent portion 28a carries the debris away. Similar to the pre-cleaning portion 24a and cleaning portion 26a, the absorbent portion 28a can be rinsed to remove all debris from the pad 28a. Additionally, the absorbent portion 28a can be saturated in a medication, antiseptic or other cleansing solution and utilized as an applicator to apply solutions to the tongue's upper surface.

Figure 6:
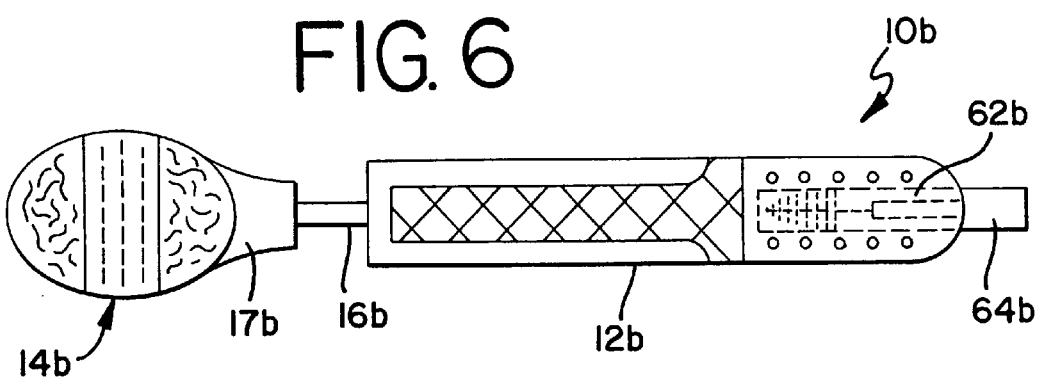
FIG. 6 is a plan view of an underside of an oral cleaning apparatus according to a third embodiment of the present invention.
Figure 7:
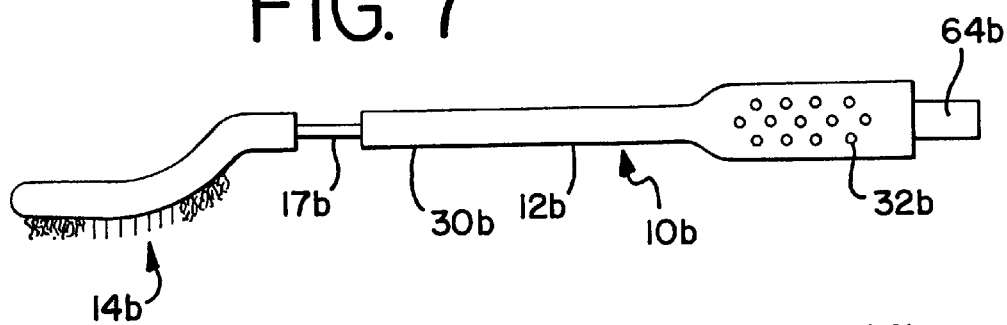
FIG. 7 is a side elevation view of the oral cleaning apparatus illustrated in FIG. 6.
Figure 8:
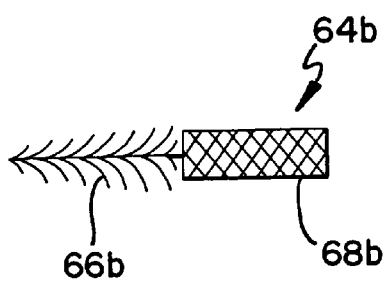
FIG. 8 is a elevation view of a utensil utilized with the oral cleaning apparatus illustrated in FIGS. 6 and 7.

With reference to FIGS. 6 and 7, in a third embodiment of the present invention, the oral cleaning apparatus 10b has a modified handle 12b. The handle 12b is modified to include a storage cavity 62b. The storage cavity 62b is a hollowed out portion of the handle 12b which is capable of removably retaining a dental hygiene utensil 64b (e.g., a pick, brush or gum massager formed from semi-firm nylon or rubber). A typical dental hygiene utensil 64b is illustrated in FIG. 8 and comprised of a brush 66b connected to an extension 68b. The brush 66b is similar in design and application to the interproximal brush 34 of the first embodiment of FIG. 1. This utensil 64b, however, unlike brush 34, is not integral to the handle 12b and is disposable, not permanent. As such, utensil 64b can be removed from the cavity 62b by the user and manipulated appropriately to generally clean and remove particles between the user's teeth. Following usage, the utensil 64b can be re-inserted into the cavity 62b for storage. Additionally, the utensil 64b can be screwed to, snap fit to, or frictionally attached to the cavity so that it stays in place when not being used.

Figure 9:
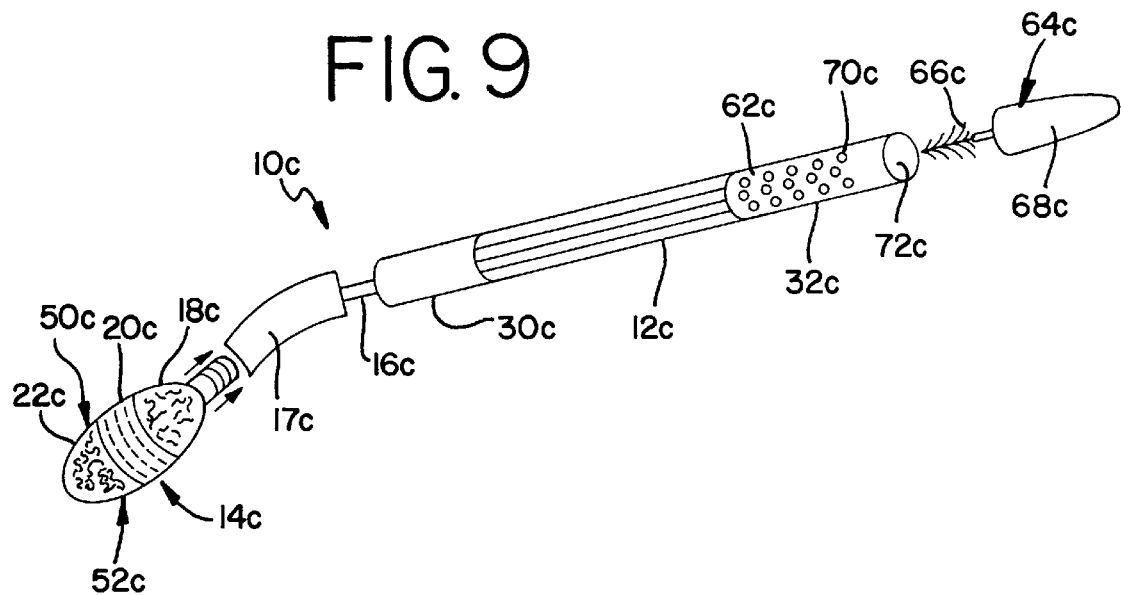
FIG. 9 is a perspective view of an oral cleaning apparatus according to a fourth embodiment of the present invention.

Referring to FIG. 9, in a fourth embodiment of the oral cleaning apparatus 10c of the present invention, the oral cleaning apparatus 10c is comprised of an elongated handle 12c and a head component 14c. The elongated handle 12c has a proximal end 30c and a distal end 32c. The elongated handle 12c of this embodiment is generally cylindrical in shape and is partially hollow, defining a cavity 62c.

An opening 72c to the hollow cavity 62c is adjacent the distal end 32c of the handle 12c. The entrance to the cavity 62c may have threads or connecting means (not shown) which allow a dental hygiene utensil 64c to be attached thereto. In that regard, the brush portion 66c of the utensil 64c extends into the cavity 62c and the extension portion 68c screws into, snaps into or is fixed to the walls of the cavity 62c entrance 72c. The brush portion 66c of the utensil 64c may be disposable, i.e., removably attached to the utensil 64c. In such an embodiment, extra brush portions 66c may be stored in the cavity 62c.

The handle 12c further has vent holes 70c which extend through the outer wall of the handle 12c and into the cavity 62c. The vent holes 70c allow air to pass freely from the environment to the cavity 62c to not only dry the brush 66c, but also to maintain a cleaner environment within the cavity 62c.

Rather than being entirely rigid, the handle 12c of the embodiment illustrated in FIG. 9 has a flexible portion 16c located adjacent the most proximal end 30c of the handle 12c. The flexible portion 16c connects the handle 12c to the neck portion 17c of the head component 14c. The flexible portion 16c operates as a leaf spring or shock absorber between the neck portion 17c and the handle 12c, allowing the head component 14c to flex relative of the handle 12c.

The head component 14c has a first side 50c and a second side 52c. Both the first and second sides 50c,52c are convex in shape and include a first section 18c comprised of a pre-cleaning portion 24c, a second section 20c comprised of a deep cleaning portion 26c, and a third section 22c comprised of a final-cleaning absorbent portion 28c. Each section 18c,20c,22c is similar to their respective sections described in previous embodiments. The head component 14c is connected to the neck portion 17c. Similar to the dental hygiene utensil 64c (which screws into, snaps into, or is frictionally fixed to the entrance of the cavity 62c at the distal end 32c of the handle), the head component 14c screws into, snaps into, or is fixed to the neck portion 17c. The embodiment illustrated in FIG. 9 shows the head component 14c removed from the neck portion 17c. The connection between the handle 12c and the head component 14c allows the head component 14c to rotate 180° such that both the first side 50c and the second side 52c can be utilized for cleaning purposes.

Figure 10:
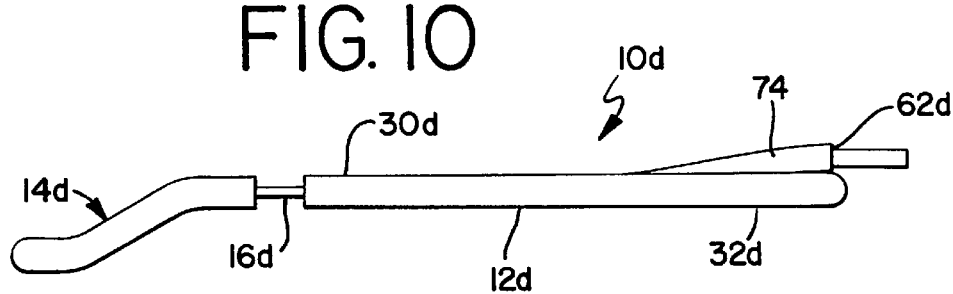
FIG. 10 is a side elevation view of an oral cleaning apparatus according to a fifth embodiment of the present invention.

Referring now to FIG. 10, a fifth embodiment of the oral cleaning apparatus 10d of the present invention is illustrated. This embodiment is similar to the embodiment illustrated in FIGS. 5 and 6 in that it comprises a handle 12d, a head component 14d and a flexible connector 16d. The handle 12d is modified however to include a housing 74 on a surface near the distal end 32d. The housing 74 defines a cavity 62d which houses a dental hygiene utensil 64d. The entrance 72d to the housing 74 may be threaded to allow a dental hygiene utensil 64d to be attached thetto (or the utensil 64d may be snap fitted or frictionally fitted in the housing 74). Optionally, the housing 74 may include vent holes (not shown) which extend into the cavity 62d for the purposes described above.

Figure 11:
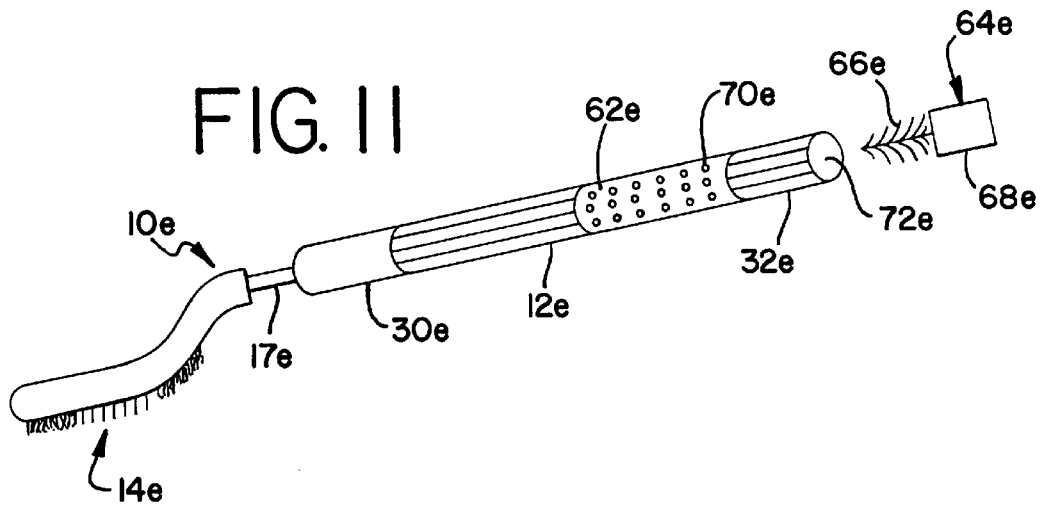
FIG. 11 is a perspective view of an oral cleaning apparatus according to a sixth embodiment of the present invention.

The final embodiment illustrated in FIG. 11 combines a generally cylindrical handle 12e with a head component 14e similar to the head component 14 disclosed in FIGS. 2, 5–7 and 10. The handle 12e includes a cavity 62e which receives utensil 64e. The cavity includes vent holes 70e. The utensil 64e can be affixed in the cavity as previously described. The head component 14e is connected to the handle 12e via flexible connector 17e and consists of three sections comprised of a pre-cleaning portion, a deep cleaning portion and a final cleaning absorbent portion, respectively.

While the specific embodiments have been illustrated and described, numerous modifications come to mind without significantly departing from the spirit of the invention, and the scope of protection is only limited by the scope of the accompanying Claims.

I claim:

1. An oral cleaning apparatus for cleaning the surface of the tongue, the apparatus comprising:

an elongated handle;

a head component having a cleaning surface with a convex portion thereto, a first section and a second section on the cleaning surface, the first section being comprised of a cleaning portion and the second section being comprised of an absorbent portion; and, a flexible member connecting the elongated handle and the head component.

2. The oral cleaning apparatus of claim 1, wherein the head component further has a third section on the cleaning surface, the third section being comprised of a pre-cleaning portion.

3. The oral cleaning apparatus of claim 1, wherein the flexible member allows for variable pressure to be exerted on the tongue by the apparatus.

4. The oral cleaning apparatus of claim 1, wherein the handle has an integral brush extending substantially perpendicular from the handle.

5. The oral cleaning apparatus of claim 1, wherein the handle has an integral gum massager extending therefrom.

6. The oral cleaning apparatus of claim 1, wherein the handle has a roughened surface for gripping the apparatus.

7. The oral cleaning apparatus of claim 1, wherein the handle includes multiple flat surfaces for gripping the apparatus.

8. The oral cleaning apparatus of claim 1, wherein the cleaning portion comprises a hook material.

9. The oral cleaning apparatus of claim 1, wherein the absorbent portion comprises a material selected from the group consisting of gauze, cotton, and reticulated polyurethane.

10. The oral cleaning apparatus of claim 2, wherein the pre-cleaning portion comprises an abrasive fabric.

11. The oral cleaning apparatus of claim 2, wherein the pre-cleaning portion comprises a hook material.

12. The oral cleaning apparatus of claim 1, wherein the cleaning portion comprises a plurality of projections extending from the head component.

13. The oral cleaning apparatus of claim 1, wherein the head component is removably attached to the flexible connector.

14. An oral cleaning apparatus for cleaning and removing particles from the surface of the tongue, the apparatus comprising:

an elongated handle;

a brush connected to the handle;

a head component having a first side with a convex portion thereto and a second side, the first side comprised of a pre-cleaning pad, cleaning projections, and an absorbent pad; and, a flexible member connecting the elongated handle and the head component.

15. The oral cleaning apparatus of claim 14, wherein the handle has a roughened surface for gripping the apparatus.

16. The oral cleaning apparatus of claim 14, wherein the handle includes multiple flat surfaces for gripping the apparatus.

17. The oral cleaning apparatus of claim 14, wherein the pre-cleaning pad is comprised of a material having a plurality of loops.

18. The oral cleaning apparatus of claim 14, wherein the cleaning projections are comprised of a plurality of flexible projections extending from the head component.

19. The oral cleaning apparatus of claim 14, wherein the cleaning projections are integral with the head component.

20. The oral cleaning apparatus of claim 14, wherein the absorbent pad comprises a material selected from the group consisting of gauze, cotton, and reticulated polyurethane.

21. The oral cleaning apparatus of claim 14, wherein the head component is removably connected to the flexible member.

\* \* \* \* \*